US005854221A

United States Patent [19]
Cao et al.

[11] Patent Number: 5,854,221
[45] Date of Patent: Dec. 29, 1998

[54] ENDOTHELIAL CELL PROLIFERATION INHIBITOR AND METHOD OF USE

[75] Inventors: Yihai Cao, Stockholm, Sweden; M. Judah Folkman, Brookline; Michael S. O'Reilly, Winchester, both of Mass.

[73] Assignee: The Children's Medical Center Corporation, Boston, Mass.

[21] Appl. No.: 763,528

[22] Filed: Dec. 12, 1996

Related U.S. Application Data

[60] Provisional application No. 60/008,519 Dec. 13, 1995.
[51] Int. Cl.$^6$ ............................ A61K 38/00; C07K 14/00
[52] U.S. Cl. ............................ 514/12; 530/350; 530/380
[58] Field of Search .............................. 514/12; 530/350, 530/380

[56] References Cited

U.S. PATENT DOCUMENTS 5,639,725  6/1997  O'Reilly et al. ........................ 514/12

FOREIGN PATENT DOCUMENTS

| 58-036391 | 3/1983 | Japan . |
| WO 91/10424 | 7/1991 | WIPO . |
| WO 93/1671 | 9/1993 | WIPO . |
| WO 95/25543 | 9/1995 | WIPO . |
| WO 95/29242 | 11/1995 | WIPO . |

OTHER PUBLICATIONS

Wu et al., Biochem. Biophys Res. Comm. vol. 188, No. 1 (Oct. 1992) pp.703–711.
Wu et al., J. Biol. Chem. vol. 265 No. 32 Nov. 1990 pp. 19658–19664.
Petersen et al., J. Biol. Chem. vol. 265 No. 11 Apr. 1990 pp. 6104–6111.
McCance, S.G. et al., "Amino Acid Residues of the Kringle–4 and Kringle–5 Domains of Human Plasminogen That Stabilize Their Interactions with ω–Amino Acid Ligands", The Journal of Biological Chemistry, vol. 269, No. 51, Issue of Dec. 23, pp. 32405–32410, 1994.
Church, W.R. et al., "A Kringle–Specific Monoclonal Antibody", Hybridoma, vol. 13, No. 5, pp. 423–429, Oct. 1994.
Abe, N. et al., "Identification of a Novel Collagen Chain Represented by Extensive Interruptions in the Triple–Helical Region", Biochem. and Biophy. Resch. Comm., vol. 196, No. 2, pp. 576–582 (1993).
Algire, G.H. et al., "Vascular reactions of normal and malignant tumors in vivo. I. Vascular reactions of mice to wounds and to normal and neoplastic transplants", J. Natl. Canc. Inst., vol. 6, pp. 73–85 (1945).
Angiolillo, A.l. et al., "Human interferon–inducible Protein 10 is a potent inhibitor of angiogenesis in vivo", J. Exp. Med., vol. 182, pp. 155–162 (1995).
Brem, H. et al., "Interstitial chemotherapy with drug polymer implants for the treatment of recurrent gliomas", J. Neurosurg., vol. 74, pp. 441–446 (1991).
Brockway, W.J. et al., "Measurement of the Binding of Antifibrinolytic Amino Acids to Various Plasminogens", Arch. Biochem. Biophys., vol. 151, pp. 194–199 (1972).
Browne, M.J. et al., "Expression of Recombinant Human Plasminogen and Aglycoplasminogen in HeLa Cells", Fibrinolysis, vol. 5, pp. 257–260 (1991).
Cao, Y. et al., "gro–β,α–C–X–C– Chemokine, Is an Angiogenesis Inhibitor That Suppresses the Growth of Lewis Lung Carcinoma in Mice", J. Esp. Med., vol. 182, pp. 2069–2077 (1995).
Chen, C. et al., "A Strategy to Discover Circulating Angiogenesis Inhibitors Generated by Human Tumors", Canc Resch., vol. 55, pp. 4230–4233 (1995).
Clapp, c. et al., "The 16–kilodalton N–terminal fragment of human proclactin is a potet inhibitor of angiogenesis", Endocrinology, vol. 133, pp. 1292–1299 (1993).
Cleary, S. Mulkerrin et al., "Purification ad Characteirzation of Tissue Plasminogen Activator Kringle–$^2$ Doman Expressed in Escherichia coli", Biochem., vol. 28, pp. 1884–1891 (1989).
Dameron, K.M. et al., "Control of angiogenesis in fibroblasts by p53 regulation of thrombospondin–1", Science, vol. 265, pp. 1582–1584 (1994).
Folkman, J., "Tumor angiogenesis and tissue factor", Nature Med. vol. 2, pp. 167–168 (1996).
Folkman, J., "What is the Evidence that Tumors are Angiogenesis Dependent?", J. Natl Canc Inst., vol. 82, pp. 4–6 (1990).
Folkman, J., "Angiogenesis in cancer, vascular, rheumatoid and other disease", Nature Medicine, vol. 1, No. 1, pp. 27–31 (1995).
Folkman, J., "Long–term culture of capillary edothelial cells", Proc. Natl. Acad. Sci. USA 76, pp. 5217–5221 (1979).
Folkman, J. et al., "Induction of agiogenesis during the transition from hyperplasia to neoplasia", Nature, vol. 339, pp. 58–61 (1989).
Folkman, J. et al., "Tumor Behavior in Isolated Perfused Organs In Vitro Growth ad Metastases of Biopsy Material in Rabbit Thyroid and Canine Intestinal Segment", Annals of Surgery, vol. 164, No. 3, pp. 491–501 (1996).
Folkman, J., "Angiogenesis and Its Inhibitors", Important Advances in Oncology, J.B. Lippincott Company, pp. 42–62 (1985).
Folkman, J., "Tumor Angiogenesis Therapeutic Implications", NE J. of Med., No. 18, pp. 1182–1186 (1971).
Gavrieli, Y. et al., "Identification of programmed cell death in situ via specific labeling of uclear DNA fragmentation", J. CellBiol., vol. 119, pp. 493–501 (1992).

(List continued on next page.)

Primary Examiner—Cecilia J. Tsang
Assistant Examiner—Bennett Celsa
Attorney, Agent, or Firm—Jones & Askew

[57] ABSTRACT

The present invention comprises an endothelial inhibitor and method of use therefor. The endothelial cell proliferation inhibitor is a protein having a molecular weight of approximately 14 kD and having an amino acid sequence substantially similar to Kringle 5 of a plasminogen molecule, that has the ability to inhibit endothelial cell proliferation in in vitro assays.

25 Claims, 5 Drawing Sheets

OTHER PUBLICATIONS

Gimbrone, M.A. et al., "Tumor Growth and Neovascularization An Experimental Model using the Rabbit Cornea", *J. Natl. Canc. Inst.*, vol. 52, No. 2 pp. 413–427 (1974).

Gimbrone, M.A. et al., "Tumor Dormancy in Vivo by Prevention of Neovascularizatio", *J. of Experi. Med.*, vol. 136, pp. 261–276 (1972).

Good, D.J. et al., "A tumor suppressor–dependent inhibitor of angiogenesis is immunologically ad functionally indistinguishable from a fragment of thrombospondin", *Proc. Nat. Acad. Sci. USA*, vol. 87, pp. 6624–6628 (1990).

Grant, D.S. et al., "Scatter factor induces blood vessel formation in vivo", *Proc. Natl. Acad. Sci. USA*, vol. 99, pp. 1937–1941 (1993).

Grant, D.S. et al., "Two different laminin domains mediate the differentiation of human endothelial cells into capillary–like structures in vitro", *Cell*, vol. 58, pp. 933–943 (1989).

Gross, J.L. et al., "Modulation of Solid Tumor Growth in vivo by bFGF", *Proc. Amer. Assoc. Canc. Resh*, vol. 31, p. 79 (1990).

Gross, J.L. et al., "Increased capillary endothelial cell protease activity in response to agiogeic stimuli in vitro.", *Proc. Natl. Acad. sci. USA*, vol. 80, pp. 2623–2627 (1983).

Gunzler, W.A. et al., "The Primary Structure of High Molecular Mass Urokinase from Human Urine", *Hoppe–Seyler's Z. Physiol. Chem.*, vol. 363, pp. 1155–1165 (1982).

Gupta, S.K. et al., "A potent inhibitor of endothelial cell proliferation is generated by proteolytic cleavage of the chemokine platelet factor 4", *Proc. Natl. Acad. Sci. USA*, vol. 92, pp. 7779–7803 (1995).

Holmgren, L. et al., "Dormancy of micrometastases Balaced proliferation and apoptosis in the presence of angiogenesis suppression", *Nature Medicie*, vol. 1, No. 2, pp. 149–153 (1995).

Homandberg, G.A. et al., "Heparin–binding fragments of fibronectin are potent inhibitors of edothelial cell growth", *Am. J. Path.*, vol. 120, pp. 327–332 (1985).

Hori, A. et al., "Suppression of Solid tumor Growth by Immunoneutralizing Monoclonal Antibody against Human Basic Fibroblast Growth Factor", *Canc. Resch.*, vol. 51, pp. 6180–6184 (1991).

Ingber, D. et al., "Synthetic analogues of fumagillin that inhibit angiogenesis and suppress tumor growth", *Nature*, vol. 348, pp. 555–557 (1990).

Johansson, J. et al., "Surfactant Protein B: Disulfide Bridges, Structural Properties, and Kringle Similarities", *Biochem.*, vol. 30, pp. 6917–6921 (1991).

Kandel, J. et al., "Neovascularization is Associated with a Switch to the Export of bFGF in the Multistep Development of Fibrosarcoma", *Cell*, vol. 66, pp. 1095–1104 (1991).

Kim, K.J. et al., "Inhibition of vascular endothelial growth factor–induced angiogenesis suppresses tumor growth in vivo", *Nature*, vol. 362, pp. 841–844 (1993).

Kivirikko, S. et al., "Primary Structure of the αl Chain of Human Type XV Collagen and Exon–Intron Organization in the 3' Region of the Corresponding Gene", *J. Bio. Chem.*, vol. 269, No. 7, pp. 4773–4779 (1994).

Knighton, D. et al., "Avascular and Vascular Phases of Tumor Growth in the Chick Embryo", *Br. J. Cancer*, vol. 35, pp. 347–356 (1977).

Lein, W.M. et al., "The blood supply of experimental liver metastases. II. A Microcirculatory study of the normal and tumor vessels of the liver with the use of perfused silicone rubber", *Surgery*, vol. 68, No. 2, pp. 334–340 (1970).

Lerch et al., "Localization of Individual Lysine–Binding Regions in Human Plasminogen and Investigations on Their Complex–Forming Properties", *European Journal of Biochemistry*, vol. 107, No. 1, pp. 7–13 (1980).

Lokker, N.A. et al., "Mutational analysis and molecular modeling of the N–terminal kringle–containing domain of hepatocyte growth gactor identifies amino acid side chains important for interaction with the c–met receptor" *Prot. Engin.*, vol. 7, pp. 895–903 (1994).

Maione, T.E. et al., "Inhibition of Angiogenesis by Recombinant Human Platelet Factor–4 and Related Peptiddes", *Science*, vol. 247, pp. 77–79 (1990).

Marti, D. et al., "Expression purification and characterization of the recombinant kringle 2 and kringle 3 domains of human plasminogen and analysis of their binding affinity for ω–aminocarboxylic acids", *Eur. J. Biochem.*, vol. 219, pp. 455–462 (1994).

McLean, J.W. et al., "cDNA sequence of human apolipoprotein(a) is homologous to plasminogen", *Nature*, vol. 330, pp. 132–137 (1987).

Menhart, N. et al., "Construction Expression, and Purification of Recombinant Kringle 1 of Human Plasminogen and Analysis of Its Interaction with ω–Amino Acids", *Biochem.*, vol. 30, pp. 1948–1957 (1991).

Millauer, B. et al., "Glioblastoma growth inhibited in vivo by a dominant–negative Flk–1 mutant", *Nature*, vol. 367, pp. 576–579 (1994).

Moses, M.A. et al., "Identification of a Inhibitor of Neovascularization from Cartilage", *Science*, vol. 248 (1990).

Muragaki, Y. et al., "Mouse col 18al i expressed in a tissue–specific manner as three alternative varients and is localized in basement membrane zones", *Proc. Natl. Acad. Sci. USA*, vol. 92, pp. 8763–8767 (1995).

Muthukkaruppan, VR., "Angiogenesis in the Mouse Cornea", *Science*, vol. 205, pp. 1416–1418 (1979).

Nelson, J.A. et al., "Murine epidermal growth factor (EGF) fragment (33–42) inhibits both EGF–and laminin–dependent endothelial cell motility and angiogenesis", *Canc. Resch.*, vol. 55, pp. 3772–3776 (1995).

Nguyen, M. et al. "Quantitation of Agiogenesis and Anti–angiogenesis in the Chick Embryo Chorioallantoic Membrande", *Microvascular Research*, vol. 47, pp. 31–49 (1994).

Nguyen, M. et al., "Elevated Levels of the Angiogenic Peptide Basic Fibroblast Growth Factor in Urine of Bladder Cancer Patients", *J. of Nat. Canc. Inst.*, vol. 85, No. 3, pp. 241–242 (1993).

O'Reilly et al., "Endogeneous Inhibitors of Angiogenesis", *Proc. Am. Assoc. Canc. Resch.*, vol. 37, p. 669 (1996).

O'Reilly et al., "Angiostatin induces and sustains dormancy of human primary tumors in mice", *Nature Medicine*, vol. 2, No. 6, pp. 689–692 (1996).

O'Reilly et al., "The suppression of Tumor Metastases by a Primary Tumor", *Surgical Forum*, vol. XLIX, pp. 474–476 (1993).

O'Reilly et al., "Angiostatin A Novel Angiogenesis Inhibitor that Mediates the Suppression of Metastases by a Lewis Lung Carcinoma", *Cell*, vol. 79, pp. 315–328 (1994).

O'Reilly et al., "Angiostatin: A Circulating Endothelial Cell Inhibitor That Suppresses Angiogenesis and Tumor Growth", *Cold Spring Harbor Symposia on Quantitative Biology*, vol. LIX, pp. 471–482 (1994).

Obeso, J. et al., "Methods in Laboratory Investigation/A Hemangioendothelioma–Derived Cell Line Its Use as a Model for the Study of Endothelial Cell Biology", *Laboratory Investigation*, vol. 63, No. 2, p. 159 (1990).

Oh, S.K. et al., "Isolation and sequencing of cDNAs for proteins with multiple domains of Gly–Xaa–Yaa repeats identify a distinct family of collagenous proteins", *Proc. Natl. Acad. Sci. USA*, vol. 91, pp. 4229–4233 (1994).

Oh, S.P., "Cloning of cDNA and Geomic DNA Encoding Human Type VIII Collagen and Localization of the α(XVIII) Collagen Gene to Mouse Chromosome 10 and Human Chromosome 21", *Geomics*, vol. 19, pp. 494–499 (1994).

Parangi, S. et al, "Antiangiogenic therapy of transgenic mice impairs de novo tumor growth", *Proc. Natl. Acad. Sci. USA*, vol. 93, pp. 2002–2007 (1996).

Passaniti, A. et al., "Methods in Laboratory Investigation/A Simple, Quantitative Method for Assessing Angiogenesis and Antiangiogenic Agents Using Reconstituted Basement Membrane, Heparin, and Fibroblast Growth Factor", *Lab. Invest.*, vol. 67, No. 4, pp. 519–528 (1992).

Ponting et al., "Plasminogen: a structural review", *Blood Coagulation and Fibrinolysis*, vol. 3, pp. 605–614 (1992).

Powell, J.R. et al., "Amino Acid Sequence Analysis of the Asparagine–288 Region of the Carbohydrate Variants of Human Plasminogen", *Biochem,.* vol. 22, pp. 923–927 (1983).

Rastinejad, F. et al., "Regulation of the activity of a new inhibitor of angiogenesis by a cancer suppressor gene", *Cell*, vol. 56, pp. 345–355 (1989).

Rehn, M. et al., "α1(XVIII), a collagent chain with frequent interruptions in the collagenous sequence of distinct tissue distribution, ad homology with type XV collagen", *Proc. Natl. Acad. Sci. USA*, vol. 91, pp. 4234–4238 (1994).

Rehn, M. et al., "Identification of three N–terminal ends of type XVIII collagent chains and tissue–specifc differences in the expression of the corresponding transcripts", *J. Biol. Chem.*, vol. 270, pp. 5705–4711 (1995).

Robbins, K.C., "The Plasminogen–Plasmin Enzyme System", *Fibrinolysis*, pp. 340–357 (1987).

Sage, E.H. et al., "Inhibition Edothelial Cell Proliferation by SPARC is Mediated through a $Ca^{2+}$–Binding EF–Hand Sequence", *J. Cell. Biochem.*, vol. 57, pp. 127–140 (1995).

Sakamato, N. et al., "Inhibition of angiogenesis and tumor growth by a synthetic laminin peptide, $CDPGYIGSR-NH_2$" *Canc. Resch.*, vol. 51, pp. 903–906 (1991).

Sambrook, J. et al., "Expression of Cloned Genes in *Escherichia coli*", *Molecular Cloning Second Edition*, Cold Spring Harbor Laboratories Press, pp. 17.37–17.41.

Schaller, J. et al., "Structural Aspects of the Plasminoge of Various Species", *Enzyme*, 40 pp. 63–69 (1988).

Shi, G. et al., "Kringle Domains and Plasmin Denaturation", *Biochem. Biophy. Resch. Comm.*, vol. 178, No. 1, pp. 360–368 (1991).

Sottrup–Jensen, L. et al., "The Primary Structure of Human Plasminogen Isolation of Two Lysine–Binding Fragments and One Mini– Plasminogen (MW, 38,000) by Elastase–Catalyzed–Specific Limited Proteolysis", *Prog. in Chem. Fibrinolysis and Thrombolysis*, vol. 3, pp. 191–209 (1978).

Srivastave, A. et al., "The Prognostic Significance of Tumor-ascularity in Intermediate–Thickness (0.76–4.0mm Thick) Skin Melanoma", *Am. J. of Path.*, vol. 133, No. 2., pp. 419–424 (1988).

Strieter, R.M. et al., InterferoY–inducible protein 10 (IP–10), a member of the C–X–C chemokine family, is an inhibitor of angiogenesis. *Biochem. Biophys. Resch. Comm.*, vol. 210, pp. 51–57 (1995).

Studier, W.F. et al., "Use of T7 RNA polymerase to direct expression of cloned genes", *Methods Enzymol.*, vol. 185, pp. 60–89 (1990).

Teicher, B.A. et al., "Potentiation of cytotoxic cancer therapies by TNP–470 alone and with other antiagiogenic agents", *Int. J. Canc*, vol. 57, pp. 1–6 (1994).

Tolsma, S.S. et al., "Peptides derived from two separate domains of the matrix protein thrombospondin–1 have anti-angiogenic activity", *J. Cell Biol.*, vol. 122, pp. 497–511 (1993).

Van Meir, E. et al., "Release of an inhibitor of angiogenesis upon induction of wild type p53 expression in glioblastoma cells", *Nature Genetics*, vo. 8, pp. 171–176 (1994).

Voest, E. E. et al., "Inhibition of Angiogenesis in Vivo by Interleukin 12", *J. Nat. Can. Inst.*, vo.. 87, pp. 581–586 (1995).

Walz, D.A. et a., "Amino acid sequence of human prothrombin fragments 1 and 2", *Proc. Nat. Acad. Sci.*, vol. 74, pp. 1969–1973 (1977).

Weidner, N. et al., "Tumor Angiogenesis: A New Significant and Independent Prognostic Indicator in Early–Stage Breast Carcinoma", *J. Natl. Canc. Inst.*, vol. 84, pp. 1875–1887 (1992).

Weidner, N. et al., "Tumor Angiogenesis Correlates with Metastasis in Invasive Prostate Carcinoma", *Am. J. Path.*, vol. 143, No. 2, pp. 401–409 (1993).

Weidner, N. et al., "Tumor Angiogenesis and Metastasis— Correlation in Invasive Breast Carcinoma", *NE J. of Med.*, vol. 324, No. 1, pp. 1–8 (1991).

Wiman, B. et al., "On the Specific Interaction Between the Lysine–Binding Sites in Plasmin and Complementary Sites In $\alpha_2$–Antiplasmin and Fibrinogen", *Biochimica et Biophysica Acta.* vol. 579, pp. 142–154 (1979).

Yoshimura, T. et al., "Cloning, Sequencing, and Expression of Human Macrophage Stimulating Proteins (MSP, MST1) Confirms MSP as a Member of the Family of Kringle Proteins and Locates the MSP Gene on Chromosome 3" *Laboratory of Immunobiology*, pp. 15461–15468 (1993).

Johnstone, A. et al., "Immunochemistry in Practice", *Blackwell Scientific Publications*, Second Edition, pp. 30–47 (1987).

Menhart, N. et al., "Functional Independence of the Kringle 4 and Kringle 5 Regions of Human Plasminogen", *Biochemistry*, vol. 32, pp. 8799–8806 (1993).

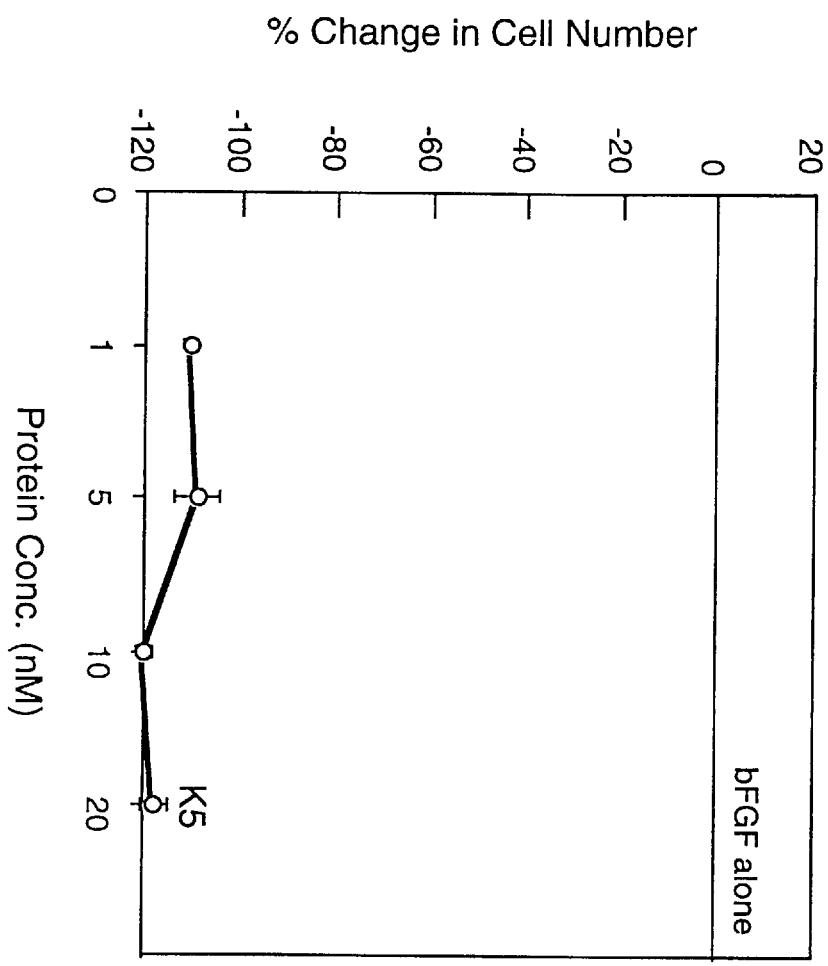

```
Kringle1  CKTGNGKNYRGTMSKTKNGITCQKWSSTSPHRP-RFSPAT
Kringle2  CMHCSGENYDGKISKTMSGLECQAWDSQSPHAHG-YIPSK
Kringle3  CLKGTGENYRGNVAVTVSGHTCQHWSAQTPHTHNR-TPEN
Kringle4  CYHGDGQSYRGTSSTTTGKKCQSWSSMTPHRHQK-TPEN
Kringle5  CMFGNGKGYRGKRATTVTGTPCQDWAAQEPHRHSIFTPET Kringle1  HPSEGLEENYCRNPDNDPQGPWCYTTDPEKRYDYCDILEC
Kringle2  FPNKNLKKNYCRNPDREL-RPWCFTTDPNKRWELCDIPRC
Kringle3  FPCKNLDENYCRNPDGKR-APWCHTTNSQVRWEYCKIPSC
Kringle4  YPNAGLTMNYCRNPDADK-GPWCFTTDPSVRWEYCNLKKC
Kringle5  NPRAGLEKNYCRNPDGDVGGPWCYTTNPRKLYDYCDVPQC
```

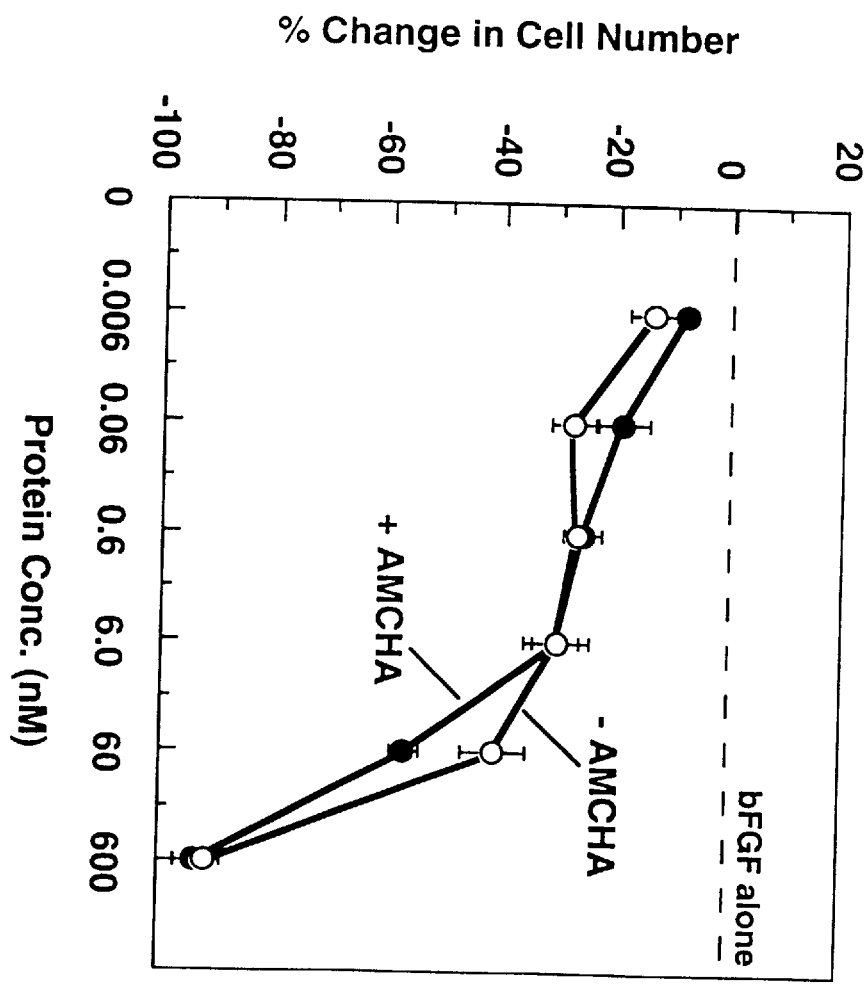
Fig_4

Inhibitory Effect of rK5 on BCE Cell Proliferation

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 79 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( x i ) SEQUENCE DESCRIPTION: SEQ ID NO:1:

```
Cys Met Phe Gly Asn Gly Lys Gly Tyr Arg Gly Lys Arg Ala Thr Thr
 1               5                  10                  15
Val Thr Gly Thr Pro Cys Gln Asp Trp Ala Ala Gln Glu Pro His Arg
            20                  25                  30
His Ser Ile Phe Thr Pro Glu Thr Asn Pro Arg Ala Gly Leu Glu Lys
        35                  40                  45
Asn Tyr Cys Arg Asn Pro Asp Gly Asp Val Gly Gly Pro Trp Cys Tyr
    50                  55                  60
Thr Thr Asn Pro Arg Lys Leu Tyr Asp Tyr Cys Asp Val Pro Gln
65                  70                  75
```

( 2 ) INFORMATION FOR SEQ ID NO:2:

( i ) SEQUENCE CHARACTERISTICS:
        ( A ) LENGTH: 79 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( i x ) FEATURE:
        ( A ) NAME/KEY: Protein
        ( B ) LOCATION: 1..79
        ( D ) OTHER INFORMATION: /note= "Kringle 1 - Figure 3"

( x i ) SEQUENCE DESCRIPTION: SEQ ID NO:2:

```
Cys Lys Thr Gly Asn Gly Lys Asn Tyr Arg Gly Thr Met Ser Lys Thr
 1               5                   10                  15

Lys Asn Gly Ile Thr Cys Gln Lys Trp Ser Ser Thr Ser Pro His Arg
            20              25                  30

Pro Arg Phe Ser Pro Ala Thr His Pro Ser Glu Gly Leu Glu Asn
        35                  40              45

Tyr Cys Arg Asn Pro Asp Asn Asp Pro Gln Gly Pro Trp Cys Tyr Thr
    50              55                  60

Thr Asp Pro Glu Lys Arg Tyr Asp Tyr Cys Asp Ile Leu Glu Cys
65              70                  75
```

(2) INFORMATION FOR SEQ ID NO:3:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (ix) FEATURE:
        (A) NAME/KEY: Protein
        (B) LOCATION: 1..78
        (D) OTHER INFORMATION: /note= "Kringle 2 - Figure 3"

(xi) SEQUENCE DESCRIPTION: SEQ ID NO:3:

```
Cys Met His Cys Ser Gly Glu Asn Tyr Asp Gly Lys Ile Ser Lys Thr
 1               5                   10                  15

Met Ser Gly Leu Glu Cys Gln Ala Trp Asp Ser Gln Ser Pro His Ala
            20              25                  30

His Gly Tyr Ile Pro Ser Lys Phe Pro Asn Lys Asn Leu Lys Lys Asn
        35                  40              45

Tyr Cys Arg Asn Pro Asp Arg Glu Leu Arg Pro Trp Cys Phe Thr Thr
    50              55                  60

Asp Pro Asn Lys Arg Trp Glu Leu Cys Asp Ile Pro Arg Cys
65              70                  75
```

(2) INFORMATION FOR SEQ ID NO:4:

(i) SEQUENCE CHARACTERISTICS:
        (A) LENGTH: 78 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: internal (ix) FEATURE:
        (A) NAME/KEY: Protein
        (B) LOCATION: 1..78
        (D) OTHER INFORMATION: /note= "Kringle 3 - Figure 3"

(xi) SEQUENCE DESCRIPTION: SEQ ID NO:4:

```
Cys Leu Lys Gly Thr Gly Glu Asn Tyr Arg Gly Asn Val Ala Val Thr
 1               5                   10                  15
```

|  |  |  |  |  |  |  |  |  |  |  |  |  |  |  |
|---|---|---|---|---|---|---|---|---|---|---|---|---|---|---|
| Val | Ser | Gly | His | Thr | Cys | Gln | His | Trp | Ser | Ala | Gln | Thr | Pro | His | Thr |
|  |  |  |  | 20 |  |  |  | 25 |  |  |  |  | 30 |  |  |
| His | Asn | Arg | Thr | Pro | Glu | Asn | Phe | Pro | Cys | Lys | Asn | Leu | Asp | Glu | Asn |
|  |  |  | 35 |  |  |  | 40 |  |  |  |  | 45 |  |  |  |
| Tyr | Cys | Arg | Asn | Pro | Asp | Gly | Lys | Arg | Ala | Pro | Trp | Cys | His | Thr | Thr |
|  |  | 50 |  |  |  | 55 |  |  |  |  |  | 60 |  |  |  |
| Asn | Ser | Gln | Val | Arg | Trp | Glu | Tyr | Cys | Lys | Ile | Pro | Ser | Cys |  |  |
| 65 |  |  |  |  | 70 |  |  |  |  | 75 |  |  |  |  |  |

( 2 ) INFORMATION FOR SEQ ID NO:5:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( i x ) FEATURE:
        ( A ) NAME/KEY: Protein
        ( B ) LOCATION: 1..78
        ( D ) OTHER INFORMATION: /note= "Kringle 4 - Figure 3"

( x i ) SEQUENCE DESCRIPTION: SEQ ID NO:5:

|  |  |  |  |  |  |  |  |  |  |  |  |  |  |  |  |
|---|---|---|---|---|---|---|---|---|---|---|---|---|---|---|---|
| Cys | Tyr | His | Gly | Asp | Gly | Gln | Ser | Tyr | Arg | Gly | Thr | Ser | Ser | Thr | Thr |
| 1 |  |  |  | 5 |  |  |  |  | 10 |  |  |  |  | 15 |  |
| Thr | Thr | Gly | Lys | Lys | Cys | Gln | Ser | Trp | Ser | Ser | Met | Thr | Pro | His | Arg |
|  |  |  | 20 |  |  |  |  | 25 |  |  |  |  | 30 |  |  |
| His | Gln | Lys | Thr | Pro | Glu | Asn | Tyr | Pro | Asn | Ala | Gly | Leu | Thr | Met | Asn |
|  |  |  | 35 |  |  |  | 40 |  |  |  |  | 45 |  |  |  |
| Tyr | Cys | Arg | Asn | Pro | Asp | Ala | Asp | Lys | Gly | Pro | Trp | Cys | Phe | Thr | Thr |
|  |  | 50 |  |  |  | 55 |  |  |  |  |  | 60 |  |  |  |
| Asp | Pro | Ser | Val | Arg | Trp | Glu | Tyr | Cys | Asn | Leu | Lys | Lys | Cys |  |  |
| 65 |  |  |  |  | 70 |  |  |  |  | 75 |  |  |  |  |  |

( 2 ) INFORMATION FOR SEQ ID NO:6:

( i ) SEQUENCE CHARACTERISTICS:
        ( A ) LENGTH: 80 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( i x ) FEATURE:
        ( A ) NAME/KEY: Protein
        ( B ) LOCATION: 1..80
        ( D ) OTHER INFORMATION: /note= "Kringle 5 - Figure 3"

( x i ) SEQUENCE DESCRIPTION: SEQ ID NO:6:

|  |  |  |  |  |  |  |  |  |  |  |  |  |  |  |  |
|---|---|---|---|---|---|---|---|---|---|---|---|---|---|---|---|
| Cys | Met | Phe | Gly | Asn | Gly | Lys | Gly | Tyr | Arg | Gly | Lys | Arg | Ala | Thr | Thr |
| 1 |  |  |  | 5 |  |  |  |  | 10 |  |  |  |  | 15 |  |
| Val | Thr | Gly | Thr | Pro | Cys | Gln | Asp | Trp | Ala | Ala | Gln | Glu | Pro | His | Arg |

|  | 20 | | | | | 25 | | | | 30 | | | |
|---|---|---|---|---|---|---|---|---|---|---|---|---|---|
| His | Ser | Ile | Phe | Thr | Pro | Glu | Thr | Asn | Pro | Arg | Ala | Gly | Leu | Glu | Lys |
| | | 35 | | | | | 40 | | | | | 45 | | | |
| Asn | Tyr | Cys | Arg | Asn | Pro | Asp | Gly | Asp | Val | Gly | Gly | Pro | Trp | Cys | Tyr |
| | 50 | | | | | 55 | | | | | 60 | | | | |
| Thr | Thr | Asn | Pro | Arg | Lys | Leu | Tyr | Asp | Tyr | Cys | Asp | Val | Pro | Gln | Cys |
| 65 | | | | | 70 | | | | | 75 | | | | | 80 |

ENDOTHELIAL CELL PROLIFERATION INHIBITOR AND METHOD OF USE

This invention may have been made with government support under National Institutes of Health grants P01-CA45548, CA64481, or HL29409. The United States Government may have certain rights in this invention.

CROSS-REFERENCE TO RELATED APPLICATIONS

The present application claims priority to U.S. Provisional Patent Application No 60/008,519 filed Dec. 13, 1995.

FIELD OF THE INVENTION

The present invention relates to a novel endothelial cell proliferation inhibitors. The inhibitor is capable of inhibiting angiogenesis related diseases and modulating angiogenic processes. In addition, the present invention relates to diagnostic assays and kits for measurement of the amount of inhibitor present in biological fluid samples, to histochemical kits for localization of the inhibitor, to DNA sequences coding for the inhibitor and molecular probes to monitor inhibitor biosynthesis and degradation, to antibodies that are specific for the inhibitor, to the development of peptide agonists and antagonists to the inhibitor's receptor, to anti-inhibitor receptor-specific antibody agonists and antagonists, and to cytotoxic agents linked to the inhibitor.

BACKGROUND OF THE INVENTION

As used herein, the term "angiogenesis" means the generation of new blood vessels into a tissue or organ, and involves endothelial cell proliferation. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels, and blood vessels.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, tumor metastasis and abnormal growth by endothelial cells and supports the pathological damage seen in these conditions. The diverse pathological disease states in which unregulated angiogenesis is present have been grouped together as angiogenic dependent or angiogenic associated diseases.

The hypothesis that tumor growth is angiogenesis-dependent was first proposed in 1971. (Folkman J., Tumor angiogenesis: Therapeutic implications., *N. Engl. Jour. Med.* 285:1182 1186, 1971) In its simplest terms it states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire G H, et al. Vascular reactions of normal and malignant tumors in vivo. I. Vascular reactions of mice to wounds and to normal and neoplastic transplants. *J. Natl. Cancer Inst.* 6:73–85, 1945)

(2) Tumors grown in isolated perfused organs where blood vessels do not proliferate are limited to 1–2 $mm^3$ but expand rapidly to >1000 times this volume when they are transplanted to mice and become neovascularized. (Folkman J, et al., Tumor behavior in isolated perfused organs: In vitro growth and metastasis of biopsy material in rabbit thyroid and canine intestinal segments. *Annals of Surgery* 164:491–502, 1966)

(3) Tumor growth in the avascular cornea proceeds slowly and at a linear rate, but switches to exponential growth after neovascularization. (Gimbrone, M. A., Jr. et al., Tumor growth and neovascularization: An experimental model using the rabbit cornea. *J. Natl. Cancer Institute* 52:41–427, 1974)

(4) Tumors suspended in the aqueous fluid of the anterior chamber of the rabbit eye, remain viable, avascular and limited in size to <1 $mm^3$. Once they are implanted on the iris vascular bed, they become neovascularized and grow rapidly, reaching 16,000 times their original volume within 2 weeks. (Gimbrone M A Jr., et al., Tumor dormancy in vivo by prevention of neovascularization. *J. Exp. Med.* 136:261–276)

(5) When tumors are implanted on the chick embryo chorioallantoic membrane, they grow slowly during an avascular phase of >72 hours, but do not exceed a mean diameter of 0.93–0.29 mm. Rapid tumor expansion occurs within 24 hours after the onset of neovascularization, and by day 7 these vascularized tumors reach a mean diameter of 8.0+2.5 mm. (Knighton D., Avascular and vascular phases of tumor growth in the chick embryo. *British J. Cancer,* 35:347–356, 1977)

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien W., et al., The blood supply of experimental liver metastases. II. A microcirculatory study of normal and tumor vessels of the liver with the use of perfused silicone rubber. *Surgery* 68:334–340, 1970)

(7) In transgenic mice which develop carcinomas in the beta cells of the pancreatic islets, pre-vascular hyperplastic islets are limited in size to <1 mm. At 6–7 weeks of age, 4–10% of the islets become neovascularized, and from these islets arise large vascularized tumors of more than 1000 times the volume of the pre-vascular islets. (Folkman J, et al., Induction of angiogenesis during the transition from hyperplasia to neoplasia. *Nature* 339:58–61, 1989)

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim K J, et al., Inhibition of vascular endothelial growth factor-induced angiogenesis suppresses tumor growth in vivo. *Nature* 362:841–844, 1993)

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori A, et al., Suppression of solid tumor growth by immunoneutralizing monoclonal antibody against human basic fibroblast growth factor. *Cancer Research*, 51:6180–6184, 1991)

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross J L, et al. Modulation of solid tumor growth in vivo by bFGF. *Proc. Amer. Assoc. Canc. Res.* 31:79, 1990)

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber D, et al., Angioinhibins: Synthetic analogues of fumagillin which inhibit angiogenesis and suppress tumor growth. *Nature*, 48:555–557, 1990). There is also indirect clinical evidence that tumor growth is angiogenesis dependent.

(12) Human retinoblastomas that are metastatic to the vitreous develop into avascular spheroids which are restricted to less than 1 mm$^3$ despite the fact that they are viable and incorporate $^3$H-thymidine (when removed from an enucleated eye and analyzed in vitro).

(13) Carcinoma of the ovary metastasizes to the peritoneal membrane as tiny avascular white seeds (1–3 mm$^3$). These implants rarely grow larger until one or more of them becomes neovascularized.

(14) Intensity of neovascularization in breast cancer (Weidner N., et al., Tumor angiogenesis correlates with metastasis in invasive breast carcinoma. *N. Engl. J. Med.* 324:1–8, 1991, and Weidner N., et al., Tumor angiogenesis: A new significant and independent prognostic indicator in early-stage breast carcinoma, *J Natl. Cancer Inst.* 84:1875–1887, 1992) and in prostate cancer (Weidner N, Carroll P R, Flax J, Blumenfeld W, Folkman J. Tumor angiogenesis correlates with metastasis in invasive prostate carcinoma. *American Journal of Pathology*, 143(2):401–409, 1993) correlates highly with risk of future metastasis.

(15) Metastasis from human cutaneous melanoma is rare prior to neovascularization. The onset of neovascularization leads to increased thickness of the lesion and an increasing risk of metastasis. (Srivastava A, et al., The prognostic significance of tumor vascularity in intermediate thickness (0.76–4.0 mm thick) skin melanoma. *Amer. J. Pathol.* 133:419–423, 1988)

(16) In bladder cancer, the urinary level of an angiogenic peptide, bFGF, is a more sensitive indicator of status and extent of disease than is cytology. (Nguyen M, et al., Elevated levels of an angiogenic peptide, basic fibroblast growth factor, in urine of bladder cancer patients. *J. Natl. Cancer Inst.* 85:241–242, 1993)

Thus, it is clear that angiogenesis plays a major role in the metastasis of a cancer. If this angiogenic activity could be repressed or eliminated, or otherwise controlled and modulated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

What is needed therefore is a composition and method which can inhibit endothelial cell proliferation such as the unwanted growth of blood vessels, especially into tumors. Also needed is a method for detecting, measuring, and localizing the composition. The composition should be able to overcome the activity of endogenous growth factors in premetastatic tumors and prevent the formation of the capillaries in the tumors thereby inhibiting the growth of the tumors. The composition, fragments of the composition, and antibodies specific to the composition, should also be able to modulate the formation of capillaries in other angiogenic processes, such as wound healing and reproduction. The composition and method for inhibiting angiogenesis should preferably be non-toxic and produce few side effects. Also needed is a method for detecting, measuring, and localizing the binding sites for the composition as well as sites of biosynthesis of the composition. The composition and fragments of the composition should be capable of being conjugated to other molecules for both radioactive and non-radioactive labeling purposes.

SUMMARY OF THE INVENTION

The present invention encompasses methods of using the isolated Kringle 5 region of plasminogen to inhibit endothelial proliferation activity. The isolated Kringle 5 peptide fragment having inhibitory activity comprises an approximately eighty (80) amino acid sequence of:

CMFGNGKGYRGKRATTVTGTPCQDWAAQEPHRHSIFTP
ETNPRAGLEKNYCRNPDGDVGGPWCYTTNPRKLYDYC
DVPQ SEQ ID NO:1

| where | C = Cys | Y = Tyr | D = Asp |
|---|---|---|---|
| | M = Met | R = Arg | W = Trp |
| | F = Phe | T = Thr | H = His |
| | G = Gly | V = Val | S = Ser |
| | N = Asn | P = Pro | I = Ile |
| | K = Lys | Q = Gln | A = Ala |
| | E = Glu | L = Leu | |

The endothelial cell proliferation peptide of the present invention corresponds to a peptide fragment generated from human plasminogen beginning at approximately amino acid 462 of human plasminogen and extending approximately 80 amino acids.

The present invention also encompasses diagnostic and therapeutic methods for detecting the presence or absence of the inhibiting peptide in body fluids, and for administration of the peptide or antibodies that specifically bind the peptide to patients in need of therapeutically effective amounts of such compounds to regulate endothelial cell proliferation. Additionally, the inhibitory peptide can be used in conjunction with in vitro proliferating endothelial cell cultures to test for compounds that mitigate the inhibitory effects of the peptide—i.e. to screen for growth factors or other compounds capable of overcoming or reversing the inhibition of endothelial cell proliferation.

Accordingly, it is an object of the present invention to provide a composition comprising a endothelial cell proliferation inhibitor comprising an approximately 80 amino acid peptide fragment of human plasminogen corresponding substantially to the Kringle 5 region beginning at amino acid 462 of human plasminogen.

It is another object of the present invention to provide a method of treating diseases and processes that are mediated by endothelial cell proliferation, especially angiogenesis.

It is yet another object of the present invention to provide a diagnostic or prognostic method and kit for detecting the presence and amount of the inhibitor in a body fluid or tissue.

It is yet another object of the present invention to provide a method and composition for treating diseases and processes that are mediated by angiogenesis including, but not limited to, hemangioma, solid tumors, leukemia, metastasis, telangiectasia, psoriasis, scleroderma, pyogenic granuloma, myocardial angiogenesis, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, Helicobacter related diseases, fractures, keloids, vasculogenesis, hematopoiesis, ovulation, menstruation, placentation, and cat scratch fever.

It is another object of the present invention to provide a composition for treating or repressing the growth of a cancer.

It is an object of the present invention to provide compounds that modulate or mimic the production or activity of enzymes that produce the inhibitor of the present invention in vivo or in vitro.

It is a further object of the present invention to provide the inhibitor or anti-inhibitor antibodies by direct injection of inhibitor DNA into a human or animal needing such treatment.

It is an object of present invention to provide a method for detecting and quantifying the presence of an antibody specific for the inhibitor in a body fluid.

It is another object of the present invention to provide a method for the detection or prognosis of cancer.

It is another object of the present invention to provide a composition for use in visualizing and quantitating sites of inhibitor binding in vivo and in vitro.

It is yet another object of the present invention to provide a composition for use in detection and quantification of inhibitor biosynthesis.

It is yet another object of the present invention to provide a therapy for cancer that has minimal side effects.

Still another object of the present invention is to provide a composition comprising the endothelial cell proliferation inhibitor of the present invention or inhibitor peptide fragment linked to a cytotoxic agent Another object of the present invention is to provide a method for targeted delivery of inhibitor-related compositions to specific locations.

Yet another object of the invention is to provide compositions and methods useful for gene therapy for the modulation of endothelial cell proliferation, such as angiogenic processes.

These and other objects, features and advantages of the present invention will become apparent after a review of the following detailed description of the disclosed embodiments and the appended claims.

BRIEF DESCRIPTION OF THE FIGURES

FIG. 1 depicts the inhibition of endothelial cell proliferation as percent change in cell number as a function of the concentration of isolated Kringle 5 peptide fragment of human plasminogen added to the cells.

Figure 2:
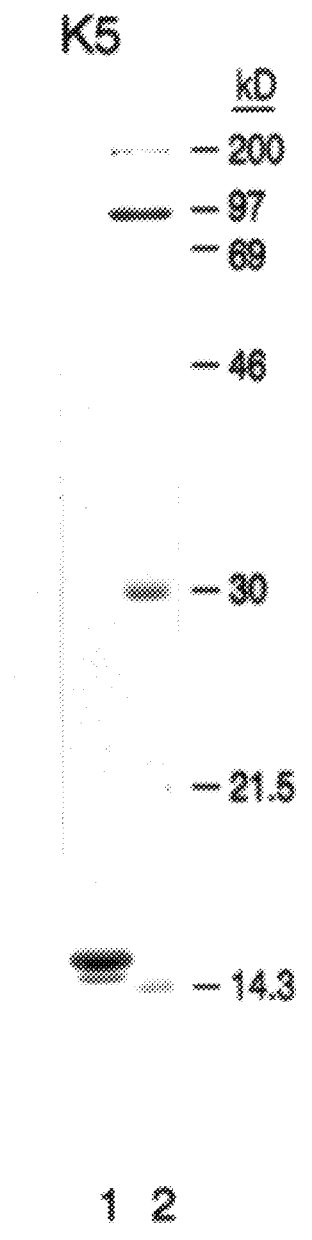

FIG. 2 shows gel electrophoresis analysis of a preparation of kringle 5 peptide fragment isolated from human plasminogen. Lane 1 is isolated Kringle 5; lane 2 is molecular weight markers.

FIG. 3 shows an amino acid composition of Kringle regions 1, 2, 3, 4, and 5 of human plasminogen.

FIG. 4 shows the anti-endothelial cell proliferation activity of human plasminogen Kringle 5, with and without amino carbonic acid (AMCHA), demonstrating that the lysine binding sites were not responsible for the anti-endothelial cell proliferation activity of Kringle 5.

DETAILED DESCRIPTION OF THE INVENTION

Figure 5:
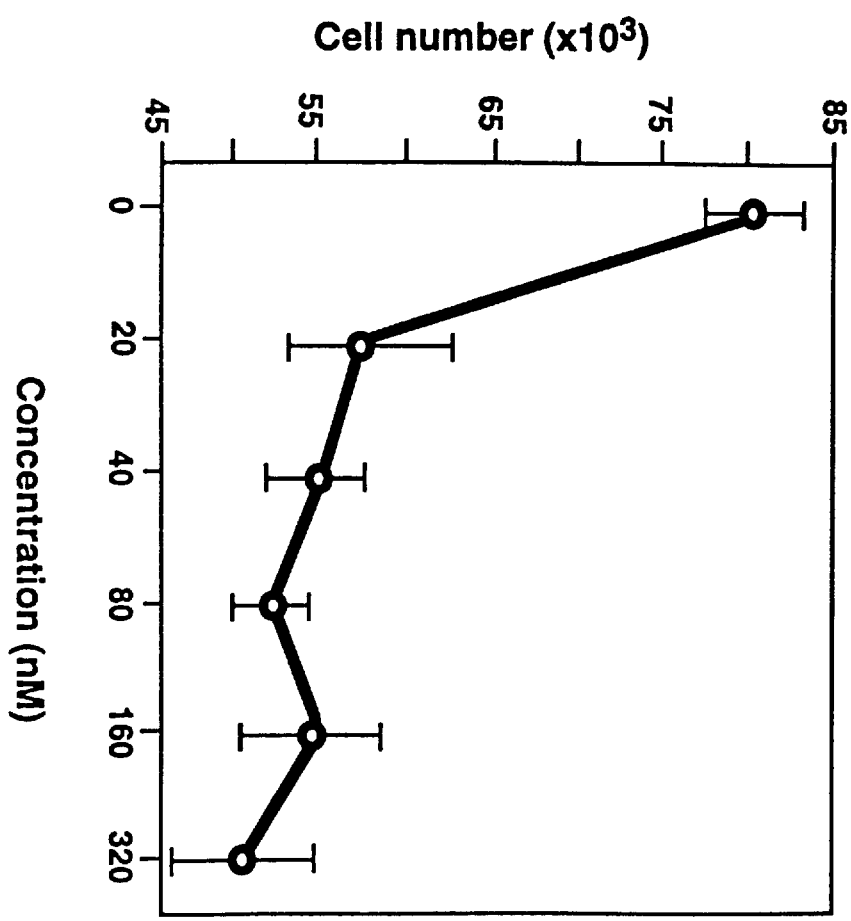
FIG. 5 shows the inhibitory effect of recombinant Kringle 5 on bovine endothelial cell proliferation.

In accordance with the present invention, compositions and methods are provided that are effective for inhibiting endothelial cell proliferation, modulating angiogenesis, and inhibiting unwanted angiogenesis, especially angiogenesis related to tumor growth. The present invention includes a protein endothelial cell proliferation inhibitor, characterized as an approximately 80 amino acid sequence derivable from human plasminogen as Kringle 5. The amino acid sequence of inhibitor may vary slightly between species. It is to be understood that the number of amino acids in the active inhibitor molecule may vary and that all closely homologous amino acid sequences that have endothelial inhibiting activity are contemplated as being included in the present invention.

The present invention provides methods and compositions for treating diseases and processes mediated by undesired and uncontrolled epithelial cell proliferation, such as angiogenesis, by administering to a human or animal having undesired endothelial cell proliferation a composition comprising approximately Kringle 5 of human plasminogen capable of inhibiting endothelial cell proliferation in in vitro assays. Desirably the isolated protein is at least approximately 80% pure, more desirably at least approximately 90% pure, even more desirable at least approximately 95% pure. The present invention is particularly useful for treating, or for repressing the growth of, tumors. Administration of the inhibitor to a human or animal with prevascularized metastasized tumors helps prevent the growth or expansion of those tumors.

The present invention also encompasses DNA sequences encoding the endothelial cell proliferation inhibitor, expression vectors containing DNA sequences encoding the endothelial cell proliferation inhibitor, and cells containing one or more expression vectors containing DNA sequences encoding the inhibitor. The present invention further encompasses gene therapy methods whereby DNA sequences encoding the endothelial cell proliferation inhibitor are introduced into a patient to modify in vivo inhibitor levels.

The present invention also includes diagnostic methods and kits for detection and measurement of the endothelial cell proliferation inhibitor in biological fluids and tissues, and for localization of the inhibitor in tissues and cells. The diagnostic method and kit can be in any configuration well known to those of ordinary skill in the art. The present invention also includes antibodies specific for the endothelial cell proliferation inhibitor and portions thereof, and antibodies that inhibit the binding of antibodies specific for the endothelial cell proliferation inhibitor. These antibodies can be polyclonal antibodies or monoclonal antibodies. The antibodies specific for the endothelial cell proliferation inhibitor can be used in diagnostic kits to detect the presence and quantity of the inhibitor which is diagnostic or prognostic for the occurrence or recurrence of cancer or other disease mediated by angiogenesis. Antibodies specific for the endothelial cell proliferation inhibitor may also be administered to a human or animal to passively immunize the human or animal against the inhibitor, thereby reducing angiogenic inhibition.

The present invention also includes diagnostic methods and kits for detecting the presence and quantity of antibodies that bind the endothelial cell proliferation inhibitor in body fluids. The diagnostic method and kit can be in any configuration well known to those of ordinary skill in the art.

The present invention also includes anti-inhibitor receptor-specific antibodies that bind to the inhibitor's receptor and transmit the appropriate signal to the cell and act as agonists or antagonists.

The present invention also includes inhibitor peptide fragments and analogs that can be labeled isotopically or with other molecules or proteins for use in the detection and visualization of the inhibitor binding sites with techniques, including, but not limited to, positron emission tomography, autoradiography, flow cytometry, radioreceptor binding assays, and immunohistochemistry.

These inhibitor peptides and analogs also act as agonists and antagonists at the inhibitor receptor, thereby enhancing or blocking the biological activity of the endothelial cell proliferation inhibitor. Such peptides are used in the isolation of the receptor molecules capable of specifically binding to the inhibitor.

The present invention also includes the endothelial cell proliferation inhibitor, inhibitor fragments, antisera specific for the inhibitor, and inhibitor receptor agonists and receptor antagonists linked to cytotoxic agents for therapeutic and research applications. Still further, the inhibitor, fragments thereof, antisera specific therefore, inhibitor receptor agonists and inhibitor receptor antagonists are combined with pharmaceutically acceptable excipients, and optionally sustained-release compounds or compositions, such as biodegradable polymers and matrices, to form therapeutic compositions.

The present invention includes molecular probes for the ribonucleic acid and deoxyribonucleic acid involved in transcription and translation of the endothelial cell proliferation inhibitor. These molecular probes are useful for detecting and measuring inhibitor biosynthesis in tissues and cells.

More particularly the present invention includes compositions and methods for the detection and treatment of diseases and processes that are mediated by or associated with endothelial cell proliferation, such as angiogenesis. The isolated Kringle 5 peptide fragment having inhibitory activity comprises an approximately eighty (80) amino acid sequence of:

---

CMFGNGKGYRGKRATTVTGTPCQDWAAQEPHRHSIFTP
ETNPRAGLEKNYCRNPDGDVGGPWCYTTNPRKLYDYC
DVPQA SEQ ID NO:1

| where | C = Cys | Y = Tyr | D = Asp |
|---|---|---|---|
| | M = Met | R = Arg | W = Trp |
| | F = Phe | T = Thr | H = His |
| | G = Gly | V = Val | S = Ser |

-continued

CMFGNGKGYRGKRATTVTGTPCQDWAAQEPHRHSIFTP
ETNPRAGLEKNYCRNPDGDVGGPWCYTTNPRKLYDYC
DVPQA SEQ ID NO:1

| N = Asn | P = Pro | I = Ile |
|---|---|---|
| K = Lys | Q = Gln | A = Ala |
| E = Glu | L = Leu | |

---

The inhibitor can be isolated from plasminogens, such as human plasminogen, or synthesized by chemical or biological methods (e.g. cell culture, recombinant gene expression, peptide synthesis, and in vitro enzymatic catalysis of plasminogen or plasmin to yield active inhibitor). Recombinant techniques include gene amplification from DNA sources using the polymerase chain reaction (PCR), and gene amplification from RNA sources using reverse transcriptase/PCR.

The present invention also encompasses a composition comprising, a vector containing a DNA sequence encoding the endothelial cell proliferation inhibitor, wherein the vector is capable of expressing the inhibitor when present in a cell, a composition comprising a cell containing a vector, wherein the vector contains a DNA sequence encoding the inhibitor or fragments or analogs thereof, and wherein the vector is capable of expressing the inhibitor when present in the cell, and a method comprising, implanting into a human or non-human animal a cell containing a vector, wherein the vector contains a DNA sequence encoding the inhibitor, wherein the vector is capable of expressing the inhibitor when present in the cell.

The term "substantially similar" or "substantially homologous" when used in reference to the inhibitor amino acid and nucleic acid sequences, means an amino acid sequence having endothelial cell proliferation inhibiting activity and having a molecular weight of approximately 14 kD, which also has a high degree of sequence homology to the protein having the specific Kringle 5 amino acid sequence disclosed herein, or a nucleic acid sequence that codes for an endothelial cell proliferation inhibitor having a molecular weight of approximately 14 kD and a high degree of homology to the amino acid having the specific Kringle 5 amino acid sequence disclosed herein.

A high degree of homology means at least approximately 80% amino acid homology, desirably at least approximately 90% amino acid homology, and more desirably at least approximately 95% amino acid homology. The term "endothelial inhibiting activity" as used herein means the capability of a molecule to inhibit angiogenesis in general and, for example, to inhibit the growth of bovine capillary endothelial cells in culture in the presence of fibroblast growth factor.

The present invention also includes the detection of the inhibitor in body fluids and tissues for the purpose of diagnosis or prognosis of diseases such as cancer. The present invention also includes the detection of inhibitor binding sites and receptors in cells and tissues. The present invention also includes methods of treating or preventing angiogenic diseases and processes including, but not limited to, arthritis and tumors by stimulating the production of the inhibitor, and/or by administering isolated inhibitor, or desirable purified inhibitor, or inhibitor agonists or antagonists, and/or inhibitor-specific antisera or antisera directed against inhibitor-specific antisera to a patient. Additional treatment methods include administration of the inhibitor, biologically active fragments thereof, inhibitor analogs, inhibitor-specific antisera, or inhibitor receptor agonists and antagonists linked to cytotoxic agents.

Passive antibody therapy using antibodies that specifically bind the inhibitor can be employed to modulate angiogenic-dependent processes such as reproduction, development, and wound healing and tissue repair. In addition, antisera directed to the Fab regions of inhibitor-specific antibodies can be administered to block the ability of endogenous inhibitor-specific antisera to bind inhibitor.

The present invention also encompasses gene therapy whereby the gene encoding the inhibitor is regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn. 12(4): 335–356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies such as identifying the defective gene and then adding a functional gene to either replace the function of the defective gene or to augment a slightly functional gene; or prophylactic strategies, such as adding a gene for the product protein that will treat the condition or that will make the tissue or organ more susceptible to a treatment regimen. As an example of a prophylactic strategy, a nucleic acid sequence coding for the inhibitor may be placed in a patient and thus prevent occurrence of angiogenesis; or a gene that makes tumor cells more susceptible to radiation could be inserted and then radiation of the tumor would cause increased killing of the tumor cells.

Many protocols for transfer of inhibitor DNA or inhibitor regulatory sequences are envisioned in this invention. Transfection of promoter sequences, other than one normally found specifically associated with the inhibitor, or other sequences which would increase production of the inhibitor protein are also envisioned as methods of gene therapy. An example of this technology is found in Transkaryotic Therapies, Inc., of Cambridge, Mass., using homologous recombination to insert a "genetic switch" that turns on an erythropoietin gene in cells. See Genetic Engineering News, Apr. 15, 1994. Such "genetic switches" could be used to activate the inhibitor (or the inhibitor receptor) in cells not normally expressing the inhibitor (or the receptor for the inhibitor).

Gene transfer methods for gene therapy fall into three broad categories-physical (e.g., electroporation, direct gene transfer and particle bombardment), chemical (lipid-based carriers, or other non-viral vectors) and biological (virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupffer cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer, and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using virally mediated gene transfer using a noninfectious virus to deliver the gene in the patient or injecting naked DNA into a site in the patient and the DNA is taken up by a percentage of cells in which the gene product protein is expressed. Additionally, the other methods described herein, such as use of a "gene gun," may be used for in vitro insertion of endothelial cell proliferation inhibitor DNA or inhibitor regulatory sequences.

Chemical methods of gene therapy may involve a lipid based compound, not necessarily a liposome, to ferry the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and enveloping and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA.

Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as polio virus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol, and env genes enclosed at by the 5' and 3' long terminal repeats (LTR). Retroviral vector systems exploit the fact that a minimal vector containing the 5' and 3' LTRs and the packaging signal are sufficient to allow vector packaging, infection and integration into target cells providing that the viral structural proteins are supplied in trans in the packaging cell line. Fundamental advantages of retroviral vectors for gene transfer include efficient infection and gene expression in most cell types, precise single copy vector integration into target cell chromosomal DNA, and ease of manipulation of the retroviral genome.

The adenovirus is composed of linear, double stranded DNA complexed with core proteins and surrounded with capsid proteins. Advances in molecular virology have led to the ability to exploit the biology of these organisms in order to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun," and inorganic chemical approaches such as calcium phosphate transfection. Another method, ligand-mediated gene therapy, involves complexing the DNA with specific ligands to form ligand-DNA conjugates, to direct the DNA to a specific cell or tissue.

It has been found that injecting plasmid DNA into muscle cells yields high percentage of the cells which are transfected and have sustained expression of marker genes. The DNA of the plasmid may or may not integrate into the genome of the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent, transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer methods were first used in transforming plant tissue. With a particle bombardment device, or "gene gun," a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA complex can be conveniently introduced into body fluids or the bloodstream and then site specifically directed to the target organ or tissue in the body. Both liposomes and polycations, such as polylysine, lipofectins or cytofectins, can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoportein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Gene regulation of the inhibitor of the present invention may be accomplished by administering compounds that bind to the gene for the inhibitor, or control regions associated with the gene, or its corresponding RNA transcript to modify the rate of transcription or translation. Additionally, cells transfected with a DNA sequence encoding the inhibitor may be administered to a patient to provide an in vivo source of inhibitor. For example, cells may be transfected with a vector containing a nucleic acid sequence encoding the inhibitor.

The term "vector" as used herein means a carrier that can contain or associate with specific nucleic acid sequences, which functions to transport the specific nucleic acid sequences into a cell. Examples of vectors include plasmids and infective microorganisms such as viruses, or non-viral vectors such as ligand-DNA conjugates, liposomes, lipid-DNA complexes. It may be desirable that a recombinant DNA molecule comprising an endothelial cell proliferation inhibitor DNA sequence is operatively linked to an expression control sequence to form an expression vector capable of expressing the inhibitor. The transfected cells may be cells derived from the patient's normal tissue, the patient's diseased tissue, or may be non-patient cells.

For example, tumor cells removed from a patient can be transfected with a vector capable of expressing the inhibitor protein of the present invention, and re-introduced into the patient. The transfected tumor cells produce levels of inhibitor in the patient that inhibit the growth of the tumor. Patients may be human or non-human animals. Additionally, inhibitor DNA may be directly injected, without the aid of a carrier, into a patient. In particular, inhibitor DNA may be injected into skin, muscle or blood.

Inhibitor expression may continue for a long-period of time or inhibitor DNA may be administered periodically to maintain a desired level of the inhibitor protein in the cell, the tissue or organ or biological fluid.

Although not wanting to be bound by the following hypothesis, it is believed that when a tumor becomes angiogenic it releases one or more angiogenic peptides (e.g., aFGF, bFGF, VEGF, IL-8, GM-CSF, etc.), which act locally, target endothelium in the neighborhood of a primary tumor from an extravascular direction, and do not circulate (or circulate with a short half-life). These angiogenic peptides must be produced in an amount sufficient to overcome the action of endothelial cell inhibitor (inhibitors of angiogenesis) for a primary tumor to continue to expand its population. Once such a primary tumor is growing well, it continues to release endothelial cell inhibitors into the circulation. According to this hypothesis, these inhibitors act remotely at a distance from the primary tumor, target capillary endothelium of a metastasis from an intravascular direction, and continue to circulate. Thus, just at the time when a remote metastasis might begin to initiate angiogenesis, the capillary endothelium in its neighborhood could be inhibited by incoming inhibitor.

Production of the endothelial cell proliferation inhibitor of the present invention is accomplished using similar techniques can be accomplished using recombinant DNA techniques including the steps of (1) identifying and purifying the inhibitor as described herein and exemplified by the Figures, (2) determining the N-terminal amino acid sequence of the purified inhibitor, (3) synthetically generating 5' and 3' DNA oligonucleotide primers for the inhibitor sequence, (4) amplifying the inhibitor gene sequence using polymerase, (5) inserting the amplified sequence into an appropriate vector such as an expression vector, (6) inserting the gene containing vector into a microorganism or other expression system capable of expressing the inhibitor gene, and (7) isolating the recombinantly produced inhibitor. Appropriate vectors include viral, bacterial and eukaryotic (such as yeast) expression vectors. The above techniques are more fully described in laboratory manuals such as "Molecular Cloning: A Laboratory Manual" Second Edition by Sambrook et al., Cold Spring Harbor Press, 1989, which is incorporated herein by reference Yet another method of producing the inhibitor, or biologically active fragments thereof, is by peptide synthesis. The amino acid sequence of the inhibitor can be determined, for example by automated peptide sequencing methods. Alternatively, once the gene or DNA sequence which codes for inhibitor is isolated, for example by the methods described above, the DNA sequence can be determined using manual or automated sequencing methods well know in the art. The nucleic acid sequence in turn provides information regarding the amino acid sequence.

Once the amino acid sequence of the peptide is known, peptide fragments can be synthesized by techniques well known in the art, as exemplified by "Solid Phase Peptide Synthesis: A Practical Approach" E. Atherton and R. C. Sheppard, IRL Press, Oxford, England. Multiple fragments can be synthesized which are subsequently linked together to form larger fragments. These synthetic peptide fragments can also be made with amino acid substitutions at specific locations in order to test for agonistic and antagonistic activity in vitro and in vivo. Peptide fragments that possess high affinity binding to tissues can be used to isolate receptors the bind the inhibitor on affinity columns.

The inhibitor is effective in treating diseases or processes, such as angiogenesis, that are mediated by, or involve, endothelial cell proliferation. The present invention includes the method of treating an angiogenesis mediated disease with an effective amount of inhibitor, or a biologically active fragment thereof, or combinations of inhibitor fragments that collectively possess anti-angiogenic activity, or inhibitor agonists and antagonists. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation.

The inhibitor is useful in the treatment of diseases of excessive or abnormal stimulation of endothelial cells. These diseases include, but are not limited to, intestinal adhesions, atherosclerosis, scleroderma, and hypertrophic scars, i.e., keloids. The inhibitor can be used as a birth control agent by preventing vascularization required for embryo implantation. The inhibitor is useful in the treatment of diseases that have angiogenesis as a pathologic consequence such as cat scratch disease (*Rochele minalia quintosa*) and ulcers (*Helicobacter pylori*).

The synthetic peptide fragments of the inhibitor have a variety of uses. The peptide that binds to receptor capable of binding the inhibitor with high specificity and avidity is radiolabeled and employed for visualization and quantitation of binding sites using autoradiographic and membrane binding techniques.

In addition, labeling inhibitor or peptide fragments thereof with short lived isotopes enables visualization of receptor binding sites in vivo using positron emission tomography or other modem radiographic techniques in order to locate tumors with inhibitor binding sites.

Cytotoxic agents such as ricin, are linked to the inhibitor, and high affinity peptide fragments thereof, thereby providing a tool for destruction of cells that bind the inhibitor. These cells may be found in many locations, including but not limited to, micrometastases and primary tumors. Peptides linked to cytotoxic agents are infused in a manner designed to maximize delivery to the desired location. For example, delivery may be accomplished through a cannula into vessels supplying the target site or directly into the target. Such agents are also delivered in a controlled manner through osmotic pumps coupled to infusion cannulae. A combination of inhibitor antagonists may be co-applied with stimulators of angiogenesis to increase vascularization of tissue. This therapeutic regimen provides an effective means of destroying metastatic cancer.

The inhibitor may be used in combination with other compositions and procedures for the treatment of diseases. For example, a tumor may be treated conventionally with surgery, radiation or chemotherapy combined with the inhibitor and then the inhibitor may be subsequently administered to the patient to extend the dormancy of micrometastases and to stabilize and inhibit the growth of any residual primary tumor. Additionally, the inhibitor, fragments thereof, inhibitor-specific antisera, inhibitor receptor agonists and antagonists, or combinations thereof, are combined with pharmaceutically acceptable excipients, and optionally sustained-release matrix, such as biodegradable polymers, to form therapeutic compositions.

A sustained-release matrix, as used herein, is a matrix made of materials, usually polymers, which are degradable by enzymatic or acid/base hydrolysis or by dissolution. Once inserted into the body, the matrix is acted upon by enzymes and body fluids. The sustained-release matrix desirably is chosen from biocompatible materials such as liposomes, polylactides (polylactic acid), polyglycolide (polymer of glycolic acid), polylactide co-glycolide (copolymers of lactic acid and glycolic acid) polyanhydrides, poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. A preferred biodegradable matrix is a matrix of one of either polylactide, polyglycolide, or polylactide co-glycolide (co-polymers of lactic acid and glycolic acid).

The angiogenesis-modulating therapeutic composition of the present invention may be a solid, liquid or aerosol and may be administered by any known route of administration. Examples of solid therapeutic compositions include pills, creams, and implantable dosage units. The pills may be administered orally, the therapeutic creams may be administered topically. The implantable dosage units may be administered locally, for example at a tumor site, or which may be implanted for systemic release of the therapeutic angiogenesis-modulating composition, for example subcutaneously. Examples of liquid composition include formulations adapted for injection subcutaneously, intravenously, intraarterially, and formulations for topical and intraocular administration. Examples of aerosol formulation include inhaler formulation for administration to the lungs.

The inhibitor protein of the present invention also can be used to generate antibodies that are specific for the inhibitor and its receptor. The antibodies can be either polyclonal antibodies or monoclonal antibodies. These antibodies that specifically bind to the inhibitor or inhibitor receptors can be used in diagnostic methods and kits that are well known to those of ordinary skill in the art to detect or quantify the inhibitor levels or inhibitor receptors levels in a body fluid or tissue. Results from these tests can be used to diagnose or predict the occurrence or recurrence of a cancer and other angiogenic mediated diseases.

The inhibitor also can be used to develop a diagnostic method and kit to detect and quantify antibodies capable of binding the inhibitor. These kits would permit detection of circulating inhibitor-specific antibodies. Patients that have such circulating anti-inhibitor antibodies may be more likely to develop multiple tumors and cancers, and may be more likely to have recurrences of cancer after treatments or periods of remission. The Fab fragments of these antibodies may be used as antigens to generate anti-inhibitor-specific Fab-fragment antisera which can be used to neutralize anti-inhibitor antibodies. Such a method would reduce the removal of circulating inhibitor by anti-inhibitor antibodies, thereby effectively elevating circulating inhibitor levels.

Another aspect of the present invention is a method of blocking the action of excess endogenous inhibitor. This can be done by passively immunizing a human or animal with antibodies specific for the undesired inhibitor in the system. This treatment can be important in treating abnormal ovulation, menstruation and placentation, and vasculogenesis. This provides a useful tool to examine the effects of inhibitor removal on metastatic processes. The Fab fragment of inhibitor-specific antibodies contains the binding site for inhibitor. This fragment is isolated from inhibitor-specific antibodies using techniques known to those skilled in the art. The Fab fragments of inhibitor-specific antisera are used as antigens to generate production of anti-Fab fragment serum. Infusion of this antiserum against the Fab fragments specific for the inhibitor prevents the inhibitor from binding to inhibitor antibodies. Therapeutic benefit is obtained by neutralizing endogenous anti-inhibitor antibodies by blocking the binding of inhibitor to the Fab fragments of anti-inhibitor. The net effect of this treatment is to facilitate the ability of endogenous circulating inhibitor to reach target cells, thereby decreasing the spread of metastases.

It is to be understood that the present invention is contemplated to include any derivatives of the inhibitor that have endothelial cell proliferation inhibitory activity. The present invention includes the entire inhibitor protein, derivatives of the inhibitor protein and biologically-active fragments of the inhibitor protein. These include proteins with inhibitor activity that have amino acid substitutions or have sugars or other molecules attached to amino acid functional groups. The present invention also includes genes that code for the inhibitor and the inhibitor receptor, and to proteins that are expressed by those genes.

The proteins and protein fragments with the inhibitor activity described above can be provided as isolated and substantially purified proteins and protein fragments in pharmaceutically acceptable formulations using formulation methods known to those of ordinary skill in the art. These formulations can be administered by standard routes. In general, the combinations may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. In addition, the inhibitor may be incorporated into biodegradable polymers allowing for sustained release of the compound, the polymers being implanted in the vicinity of where drug delivery is desired, for example, at the site of a tumor or implanted so that the inhibitor is slowly released systemically. Osmotic minipumps may also be used to provide controlled delivery of high concentrations of the inhibitor through cannulae to the site of interest, such as directly into a metastatic growth or into the vascular supply to that tumor. The biodegradable polymers and their use are described, for example, in detail in Brem et al., *J. Neurosurg.* 74:441–446 (1991), which is hereby incorporated by reference in its entirety.

The dosage of the inhibitor of the present invention will depend on the disease state or condition being treated and other clinical factors such as weight and condition of the human or animal and the route of administration of the compound. For treating humans or animals, between approximately 0.5 mg/kilogram to 500 mg/kilogram of the inhibitor can be administered. Depending upon the half-life of the inhibitor in the particular animal or human, the inhibitor can be administered between several times per day to once a week. It is to be understood that the present invention has application for both human and veterinary use. The methods of the present invention contemplate single as well as multiple administrations, given either simultaneously or over an extended period of time.

The inhibitor formulations include those suitable for oral, rectal, ophthalmic (including intravitreal or intracameral), nasal, topical (including buccal and sublingual), intrauterine, vaginal or parenteral (including subcutaneous, intraperitoneal, intramuscular, intravenous, intradermal, intracranial, intratracheal, and epidural) administration. The inhibitor formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, or an appropriate fraction thereof, of the administered ingredient. It should be understood that in addition to the ingredients, particularly mentioned above, the formulations of the present invention may include other agents conventional in the art having regard to the type of formulation in question. Optionally, cytotoxic agents may be incorporated or otherwise combined with inhibitor proteins, or biologically functional peptide fragments thereof, to provide dual therapy to the patient.

Angiogenesis inhibiting peptides of the present invention can be synthesized in a standard microchemical facility and purity checked with HPLC and mass spectrophotometry. Methods of peptide synthesis, HPLC purification and mass spectrophotometry are commonly known to those skilled in these arts. Inhibitor peptides and inhibitor receptors peptides are also produced in recombinant $E.$ $coli$ or yeast expression systems, and purified with column chromatography.

Different peptide fragments of the intact inhibitor molecule can be synthesized for use in several applications including, but not limited to the following; as antigens for the development of specific antisera, as agonists and antagonists active at inhibitor binding sites, as peptides to be linked to, or used in combination with, cytotoxic agents for targeted killing of cells that bind the inhibitor. The amino acid sequences that comprise these peptides are selected on the basis of their position on the exterior regions of the molecule and are accessible for binding to antisera. The amino and carboxyl termini of the inhibitor, as well as the mid-region of the molecule are represented separately among the fragments to be synthesized.

These peptide sequences are compared to known sequences using protein sequence databases such as GenBank, Brookhaven Protein, SWISS-PROT, and PIR to determine potential sequence homologies. This information facilitates elimination of sequences that exhibit a high degree of sequence homology to other molecules, thereby enhancing the potential for high specificity in the development of antisera, agonists and antagonists to the inhibitor.

Inhibitor and inhibitor derived peptides can be coupled to other molecules using standard methods. The amino and carboxyl termini of the inhibitor both contain tyrosine and lysine residues and are isotopically and nonisotopically labeled with many techniques, for example radiolabeling using conventional techniques (tyrosine residues—chloramine T, iodogen, lactoperoxidase; lysine residues—Bolton-Hunter reagent). These coupling techniques are well known to those skilled in the art. Alternatively, tyrosine or lysine is added to fragments that do not have these residues to facilitate labeling of reactive amino and hydroxyl groups on the peptide. The coupling technique is chosen on the basis of the functional groups available on the amino acids including, but not limited to amino, sulfhydral, carboxyl, amide, phenol, and imidazole. Various reagents used to effect these couplings include among others, glutaraldehyde, diazotized benzidine, carbodiimide, and p-benzoquinone.

Inhibitor peptides are chemically coupled to isotopes, enzymes, carrier proteins, cytotoxic agents, fluorescent molecules, chemiluminescent, bioluminescent and other compounds for a variety of applications. The efficiency of the coupling reaction is determined using different techniques appropriate for the specific reaction. For example, radiolabeling of an inhibitor peptide with $^{125}I$ is accomplished using chloramine T and $Na^{125}I$ of high specific activity. The reaction is terminated with sodium metabisulfite and the mixture is desalted on disposable columns. The labeled peptide is eluted from the column and fractions are collected. Aliquots are removed from each fraction and radioactivity measured in a gamma counter. In this manner, the unreacted $Na^{125}I$ is separated from the labeled inhibitor peptide. The peptide fractions with the highest specific radioactivity are stored for subsequent use such as analysis of the ability to bind to inhibitor antisera.

Another application of peptide conjugation is for production of polyclonal antisera. For example, inhibitor peptides containing lysine residues are linked to purified bovine serum albumin using glutaraldehyde. The efficiency of the reaction is determined by measuring the incorporation of radiolabeled peptide. Unreacted glutaraldehyde and peptide are separated by dialysis. The conjugate is stored for subsequent use.

Antiserum specific for the inhibitor, inhibitor analogs, peptide fragments of the inhibitor and the inhibitor receptor can be generated. After peptide synthesis and purification, both monoclonal and polyclonal antisera are raised using established techniques known to those skilled in the art. For example, polyclonal antisera may be raised in rabbits, sheep, goats or other animals. Inhibitor peptides conjugated to a carrier molecule such as bovine serum albumin, or inhibitor itself, is combined with an adjuvant mixture, emulsified and injected subcutaneously at multiple sites on the back, neck, flanks, and sometimes in the footpads. Booster injections are made at regular intervals, such as every 2 to 4 weeks. Blood samples are obtained by venipuncture, for example using the marginal ear veins after dilation, approximately 7 to 10 days after each injection. The blood samples are allowed to clot overnight at 4 C. and are centrifuged at approximately 2400×g at 4 C. for about 30 minutes. The serum is removed, aliquoted, and stored at 4 C. for immediate use or at −20 to −90 C. for subsequent analysis.

All serum samples from generation of polyclonal antisera or media samples from production of monoclonal antisera are analyzed for determination of antibody titer. Titer is established through several means, for example, using dot blots and density analysis, and also with precipitation of radiolabeled peptide-antibody complexes using protein A, secondary antisera, cold ethanol or charcoal-dextran followed by activity measurement with a gamma counter. The highest titer antisera are also purified on affinity columns which are commercially available. Inhibitor peptides are coupled to the gel in the affinity column. Antiserum samples are passed through the column and anti-inhibitor antibodies remain bound to the column. These antibodies are subsequently eluted, collected and evaluated for determination of titer and specificity.

The highest titer inhibitor-specific antisera is tested to establish the following; a) optimal antiserum dilution for highest specific binding of the antigen and lowest non-specific binding, b) the ability to bind increasing amounts of inhibitor peptide in a standard displacement curve, c) potential cross-reactivity with related peptides and proteins of related species, d) ability to detect inhibitor peptides in extracts of plasma, urine, tissues, and in cell culture media.

Kits for measurement of inhibitor, and the inhibitor receptor, are also contemplated as part of the present invention. Antisera that possess the highest titer and specificity and can detect inhibitor peptides in extracts of plasma, urine, tissues, and in cell culture media are further examined to establish easy to use kits for rapid, reliable, sensitive, and specific measurement and localization of inhibitor. These assay kits include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established. Intraassay and interassay variation is established at 20%, 50% and 80% points on the standard curves of displacement or activity.

One example of an assay kit commonly used in research and in the clinic is a radioimmunoassay (RIA) kit. An inhibitor RIA is illustrated below. After successful radioiodination and purification of inhibitor or an inhibitor peptide, the antiserum possessing the highest titer is added at several dilutions to tubes containing a relatively constant amount of radioactivity, such as 10,000 cpm, in a suitable buffer system. Other tubes contain buffer or preimmune serum to determine the non-specific binding. After incubation at 4 C. for 24 hours, protein A is added and the tubes are vortexed, incubated at room temperature for 90 minutes, and centrifuged at approximately 2000–2500×g at 4 C. to precipitate the complexes of antibody bound to labeled antigen. The supernatant is removed by aspiration and the radioactivity in the pellets counted in a gamma counter. The antiserum dilution that binds approximately 10% to 40% of the labeled peptide after subtraction of the non-specific binding is further characterized.

Next, a dilution range (approximately 0.1 pg to 10 ng) of the inhibitor peptide used for development of the antiserum is evaluated by adding known amounts of the peptide to tubes containing radiolabeled peptide and antiserum. After an additional incubation period, for example, 24 to 48 hours, protein A is added and the tubes centrifuged, supernatant removed and the radioactivity in the pellet counted. The displacement of the binding of radiolabeled inhibitor peptide by the unlabeled inhibitor peptide (standard) provides a standard curve. Several concentrations of other inhibitor peptide fragments, inhibitor from different species, and homologous peptides are added to the assay tubes to characterize the specificity of the inhibitor antiserum.

Extracts of various tissues, including but not limited to primary and secondary tumors, Lewis lung carcinoma, cultures of inhibitor producing cells, placenta, uterus, and other tissues such as brain, liver, and intestine, are prepared. After lyophilization or Speed Vac of the tissue extracts, assay buffer is added and different aliquots are placed into the RIA tubes. Extracts of inhibitor producing cells produce displacement curves that are parallel to the standard curve, whereas extracts of tissues that do not produce inhibitor do not displace radiolabeled inhibitor from the inhibitor. In addition, extracts of urine, plasma, and cerebrospinal fluid from animals with Lewis lung carcinoma are added to the assay tubes in increasing amounts. Parallel displacement curves indicate the utility of the inhibitor assay to measure inhibitor in tissues and body fluids.

Tissue extracts that contain inhibitor are additionally characterized by subjecting aliquots to reverse phase HPLC. Eluate fractions are collected, dried in Speed Vac, reconstituted in RIA buffer and analyzed in the inhibitor RIA. The maximal amount of inhibitor immunoreactivity is located in the fractions corresponding to the elution position of inhibitor.

The assay kit provides instructions, antiserum, inhibitor or inhibitor peptide, and possibly radiolabeled inhibitor and/or reagents for precipitation of bound inhibitor-inhibitor antibody complexes. The kit is useful for the measurement of inhibitor in biological fluids and tissue extracts of animals and humans with and without tumors.

Another kit is used for localization of inhibitor in tissues and cells. This inhibitor immunohistochemistry kit provides instructions, inhibitor antiserum, and possibly blocking serum and secondary antiserum linked to a fluorescent molecule such as fluorescein isothiocyanate, or to some other reagent used to visualize the primary antiserum. Immunohistochemistry techniques are well known to those skilled in the art. This inhibitor immunohistochemistry kit permits localization of inhibitor in tissue sections and cultured cells using both light and electron microscopy. It is used for both research and clinical purposes. For example, tumors are biopsied or collected and tissue sections cut with a microtome to examine sites of inhibitor production. Such information is useful for diagnostic and possibly therapeutic purposes in the detection and treatment of cancer. Another method to visualize sites of inhibitor biosynthesis involves radiolabeling nucleic acids for use in in situ hybridization to probe for inhibitor messenger RNA. Similarly, the inhibitor receptor can be localized, visualized and quantitated with immunohistochemistry techniques.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art.

EXAMPLE 1

Demonstration of Endothelial Cell Proliferation Inhibitor Activity of Kringle 5 of Human Plasminogen Source Human plasminogen is digested with appropriate enzymes to yield a Kringle 5 fragment. The peptide fragment is isolated and purified by standard methods of protein and peptide purification well known to those skilled in the art. The purity of isolated Kringle 5 is demonstrated in FIG. 2, showing the results a running the peptide preparation on gel electrophoresis.

Assay

Endothelial cell inhibitory activity was assayed by inhibition of DNA synthesis ([methyl-H$^3$] thymidine incorporation) in bovine capillary endothelial cells. Capillary endothelial cells were prepared from bovine adrenal glands and grown on gelatin-coated 48-well microtiter plates.

Varying amounts of isolated Kringle 5 are added to the cultured cells and the change in the number of cells is determined. The percent change in cell number is plotted as a function of the amount of Kringle 5 added to the cultures to yield the graph in FIG. 1.

FIG. 3 shows a comparison of similar 80 amino acid sequences derived from Kringle regions 1, 2, 3, 4, and 5 of human plasminogen.

We claim:

1. A method of inhibiting endothelial cell proliferation in vitro, comprising administering to an endothelial cell an effective amount of a protein having an amino acid sequence of a Kringle 5 peptide of a plasminogen molecule.

2. The method of claim 1, wherein the protein comprises approximately 80 amino acids.

3. The method of claim 1, wherein the protein has an amino acid sequence or SEQ ID NO:1.

4. The method of claim 1, wherein the plasminogen is human plasminogen.

5. A method of treating an individual having an angiogenesis-mediated disease comprising, administering to the individual an effective amount of a protein having an amino acid sequence of a Kringle 5 peptide of a plasminogen molecule.

6. The method of claim 5, wherein the protein comprises approximately 80 amino acids.

7. The method of claim 5, wherein the protein has an amino acid sequence or SEQ ID NO:1.

8. The method of claim 5, wherein the plasminogen is human plasminogen.

9. The method of claim 5, wherein the protein has the ability to inhibit endothelial cell proliferation.

10. The method of claim 5, wherein the angiogenesis-mediated disease is a cancer.

11. The method of claim 10, wherein the cancer is a solid tumor.

12. A method of inhibiting endothelial cell proliferation in an individual, comprising administering to the individual an effective amount of a protein having an amino acid sequence of a Kringle 5 peptide of a plasminogen molecule.

13. The method of claim 12, wherein the protein comprises approximately 80 amino acids.

14. The method of claim 12, wherein the protein has an amino acid sequence or SEQ ID NO:1.

15. The method of claim 12, wherein the plasminogen is human plasminogen.

16. The method of claim 12, wherein the individual is a human.

17. The method of claim 12, wherein the individual has an angiogenesis-mediated disease.

18. The method of claim 17, wherein the angiogenesis-mediated disease is a cancer.

19. The method of claim 18, wherein the cancer is a solid tumor.

20. The method of claim 1, wherein the protein has a molecular weight of approximately 14 kD as determined by non-reducing polyacrylamide gel electrophoresis.

21. The method of claim 5, wherein the protein has a molecular weight of approximately 14 kD as determined by non-reducing polyacrylamide gel electrophoresis.

22. The method of claim 12, wherein the protein has a molecular weight of approximately 14 kD as determined by non-reducing polyacrylamide gel electrophoresis.

23. The method of claim 1, wherein the protein has an amino acid sequence or SEQ ID NO:6.

24. The method of claim 5, wherein the protein has an amino acid sequence or SEQ ID NO:6.

25. The method of claim 12, wherein the protein has an amino acid sequence or SEQ ID NO:6.

* * * * *

UNITED STATES PATENT AND TRADEMARK OFFICE
CERTIFICATE OF CORRECTION

PATENT NO. : 5,854,221

DATED : December 29, 1998

INVENTOR(S) : Yihai Cao, et al.

It is certified that error appears in the above-identified patent and that said Letters Patent is hereby corrected as shown below:

Column 27, line 21, change "or" to --of--.

Column 27, line 32, change "or" to --of--.

Column 28, line 17, change "or" to --of--.

Column 28, line 38, change "or" to --of--.

Column 28, line 40, change "or" to --of--.

Column 28, line 42, change "or" to --of--.

Signed and Sealed this

Sixteenth Day of March, 1999

Attest:

Q. TODD DICKINSON

Attesting Officer     Acting Commissioner of Patents and Trademarks

UNITED STATES PATENT AND TRADEMARK OFFICE
Certificate

Patent No. 5,854,221                                                                Patented: December 29, 1998

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Yihai Cao, Stockholm, Sweden; M. Judah Wolkman, Brookline, MA (US); Michael S, O'Reilly, Winchester, MA (US); and Donald J. Davidson, Gurnee, IL.

Signed and Sealed this Twenty-sixth Day of February 2008.

*JULIE BURKE*
*Specialist Program Examiner*
Technology Center 1600